US009916965B2

United States Patent
Bhaskar et al.

(10) Patent No.: US 9,916,965 B2
(45) Date of Patent: Mar. 13, 2018

(54) HYBRID INSPECTORS

(71) Applicant: KLA-Tencor Corporation, Milpitas, CA (US)

(72) Inventors: Kris Bhaskar, San Jose, CA (US); Grace Hsiu-Ling Chen, Los Gatos, CA (US); Keith Wells, Santa Cruz, CA (US); Wayne McMillan, San Jose, CA (US); Jing Zhang, Santa Clara, CA (US); Scott Young, Soquel, CA (US); Brian Duffy, San Jose, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 15/394,792

(22) Filed: Dec. 29, 2016

(65) Prior Publication Data

US 2017/0194126 A1  Jul. 6, 2017

Related U.S. Application Data

(60) Provisional application No. 62/273,992, filed on Dec. 31, 2015.

(51) Int. Cl.
*G01N 21/00* (2006.01)
*H01J 37/22* (2006.01)
(Continued)

(52) U.S. Cl.
CPC ........ *H01J 37/222* (2013.01); *G01N 21/9501* (2013.01); *G01N 23/2251* (2013.01);
(Continued)

(58) Field of Classification Search
CPC ............ G03F 7/70625; G03F 7/70641; G01N 21/9501; G01N 21/8851; G06N 99/005;
(Continued)

(56) References Cited

U.S. PATENT DOCUMENTS 6,902,855 B2  6/2005  Peterson et al.
7,418,124 B2  8/2008  Peterson et al.
(Continued)

FOREIGN PATENT DOCUMENTS

WO   2015/100099   7/2015

OTHER PUBLICATIONS

International Search Report for PCT/US2016/069588 dated Apr. 12, 2017.
(Continued)

*Primary Examiner* — Kara E Geisel
*Assistant Examiner* — Maurice Smith
(74) *Attorney, Agent, or Firm* — Ann Marie Mewherter

(57) ABSTRACT

Hybrid inspectors are provided. One system includes computer subsystem(s) configured for receiving optical based output and electron beam based output generated for a specimen. The computer subsystem(s) include one or more virtual systems configured for performing one or more functions using at least some of the optical based output and the electron beam based output generated for the specimen. The system also includes one or more components executed by the computer subsystem(s), which include one or more models configured for performing one or more simulations for the specimen. The computer subsystem(s) are configured for detecting defects on the specimen based on at least two of the optical based output, the electron beam based output, results of the one or more functions, and results of the one or more simulations.

30 Claims, 2 Drawing Sheets

(51) Int. Cl.
 *G01N 21/95* (2006.01)
 *G01N 23/225* (2018.01)
 *H01J 37/06* (2006.01)
 *H01J 37/28* (2006.01)

(52) U.S. Cl.
 CPC .......... *H01J 37/06* (2013.01); *H01J 37/226* (2013.01); *H01J 37/28* (2013.01); *G01N 2201/12* (2013.01); *G01N 2223/304* (2013.01); *G01N 2223/401* (2013.01); *G01N 2223/418* (2013.01); *G01N 2223/6116* (2013.01); *G01N 2223/646* (2013.01); *H01J 2237/24475* (2013.01); *H01J 2237/24495* (2013.01); *H01J 2237/2817* (2013.01)

(58) Field of Classification Search
 CPC .. G06F 17/5009; G06T 7/0008; H01J 37/222; H01J 37/226
 See application file for complete search history.

(56) References Cited

U.S. PATENT DOCUMENTS

| | | | |
|---|---|---|---|
| 7,570,796 B2* | 8/2009 | Zafar | G03F 1/84 382/144 |
| 7,676,077 B2 | 3/2010 | Kulkarni et al. | |
| 7,729,529 B2 | 6/2010 | Wu et al. | |
| 7,769,225 B2 | 8/2010 | Kekare et al. | |
| 8,041,106 B2 | 10/2011 | Pak et al. | |
| 8,111,900 B2 | 2/2012 | Wu et al. | |
| 8,126,255 B2 | 2/2012 | Bhaskar et al. | |
| 8,213,704 B2 | 7/2012 | Peterson et al. | |
| 8,611,639 B2 | 12/2013 | Kulkarni et al. | |
| 8,664,594 B1 | 3/2014 | Jiang et al. | |
| 8,692,204 B2 | 4/2014 | Kojima et al. | |
| 8,698,093 B1 | 4/2014 | Gubbens et al. | |
| 8,716,662 B1 | 5/2014 | MacDonald et al. | |
| 9,087,176 B1* | 7/2015 | Chang | G06F 17/5081 |
| 9,098,891 B2 | 8/2015 | Kulkarni et al. | |
| 9,183,624 B2 | 11/2015 | Karsenti et al. | |
| 9,222,895 B2 | 12/2015 | Duffy et al. | |
| 2007/0285653 A1 | 12/2007 | Takahashi et al. | |
| 2008/0058978 A1* | 3/2008 | Cain | G06F 17/5009 700/121 |
| 2009/0175530 A1 | 7/2009 | Sjostrom et al. | |
| 2014/0241610 A1* | 8/2014 | Duffy | G01N 21/9501 382/149 |
| 2015/0042978 A1 | 2/2015 | Lynch | |
| 2015/0062571 A1 | 3/2015 | Kulkarni et al. | |
| 2015/0204799 A1 | 7/2015 | Cipriany et al. | |
| 2015/0324964 A1 | 11/2015 | Shifrin et al. | |
| 2016/0025648 A1 | 1/2016 | Duffy et al. | |
| 2016/0116420 A1 | 4/2016 | Duffy et al. | |
| 2016/0132695 A1 | 5/2016 | Duffy et al. | |
| 2016/0150191 A1 | 5/2016 | Karsenti et al. | |
| 2016/0209334 A1 | 7/2016 | Chen et al. | |
| 2016/0290934 A1 | 10/2016 | Wells | |
| 2016/0314578 A1 | 10/2016 | Banerjee | |
| 2016/0321800 A1 | 11/2016 | Thattaisundaram et al. | |
| 2017/0059491 A1 | 3/2017 | Duffy et al. | |
| 2017/0140524 A1 | 5/2017 | Karsenti et al. | |
| 2017/0148226 A1 | 5/2017 | Zhang et al. | |
| 2017/0161888 A1 | 6/2017 | Banerjee et al. | |
| 2017/0200265 A1 | 7/2017 | Bhaskar et al. | |

OTHER PUBLICATIONS

U.S. Appl. No. 15/176,139, filed Jun. 7, 2016 by Zhang et al. (submitted as U.S. Patent Application Publication No. 2017/0148226 published May 25, 2017 by Zhang et al.).

U.S. Appl. No. 15/353,210, filed Nov. 16, 2016 by Karsenti et al. (submitted as U.S. Patent Application Publication No. 2017/0140524 published May 18, 2017 by Karsenti et al.).

Chen et al., "Deep Learning-Based Classification of Hyperspectral Data," IEEE Journal of Selected Topics in Applied Earth Observations and Remote Sensing, vol. 7, No. 6, Jun. 2014, pp. 2094-2107.

Hand et al., "Principles of Data Mining (Adaptive Computation and Machine Learning)," MIT Press, 2001, 578 pages.

Jebara, "Discriminative, Generative, and Imitative Learning," Massachusetts Institute of Technology, MIT Thesis, Feb. 2002, 212 pages.

Kingma et al., "Semi-supervised Learning with Deep Generative Models," NIPS 2014, arXiv:1406.5298v2, Oct. 31, 2014, 9 pages.

Li et al., "Semisupervised Hyperspectral Image Segmentation Using Multinomial Logistic Regression With Active Learning," IEEE Transactions on Geoscience and Remote Sensing, vol. 48, No. 11, Nov. 2010, pp. 4085-4098.

Sugiyama, "Introduction to Statistical Machine Learning," Morgan Kaufmann, 2016, 534 pages.

* cited by examiner

HYBRID INSPECTORS

BACKGROUND OF THE INVENTION

1. Field of the Invention

The present invention generally relates to hybrid inspectors.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to drive higher yield in the manufacturing process and thus higher profits. Inspection has always been an important part of fabricating semiconductor devices. However, as the dimensions of semiconductor devices decrease, inspection becomes even more important to the successful manufacture of acceptable semiconductor devices because smaller defects can cause the devices to fail.

Currently used methods of inspection have effectively not changed for more than 20 years. Inspection solutions essentially have the following characteristics. A substantially slow electron beam type system allows a user to identify and verify problems for physical defects. Separately, a fast but coarse optical inspection is performed that covers the entire wafer, but is often limited to a single layer of inspection. These two systems are typically physically separated from each other.

Conventional lithographic scaling (at the 193 nm wavelength) appears to have stalled as of 2014-2015. It has been replaced by multi-patterning lithography processes, which appear to be here to stay for the next 10 years or so even if extreme ultraviolet (EUV) appears on the scene. Multi-patterning lithography processes have resulted in the use of an enormous number of process steps (e.g., greater than 20) just to complete a FINFET transistor whereas just a few generations ago, the conventional planar MOSFET transistor was just a few layers. In a sense, to maintain control in one dimension, complexity has been added in the z dimension. The added complexity in the z dimension has resulted in much tighter requirements for critical dimension (CD) and overlay control. Noise has increased for optical inspectors by a factor of 10× at a given layer. In fact, one can make the argument that inspection at a given layer is an ill posed problem.

There are several limitations of current stand alone optical inspectors for physical inspection. In particular, optical tools are affected by the following in the era of post CMOS scaling: post layer noise (optical systems can "see" through layers, which can be a major disadvantage if prior layers have more noise); color noise (optical systems are affected by phase changes such as local and global dimension changes in the z direction, film thickness, etc.); line edge roughness (LER), which when combined with phase based detection apertures can lead to further noise; and core resolution limitations of optics.

There are also several limitations of electron beam inspection and review tools. For example, electron beam inspectors and review platforms have the advantage of physical resolution and are increasingly being adopted but have limitations including: inability to detect process systematic defects which requires relatively wide coverage; relatively poor defect to pixel ratio for LER defects (most detection algorithms are comparison based); relatively poor defect to pixel ratio due to local charging (most detection algorithms are comparison based); and substantially limited penetration to see defects in the z direction.

Accordingly, it would be advantageous to develop systems and methods for detecting defects on a specimen that do not have one or more of the disadvantages described above.

SUMMARY OF THE INVENTION

The following description of various embodiments is not to be construed in any way as limiting the subject matter of the appended claims.

One embodiment relates to a system configured to detect defects on a specimen. The system includes an optical based subsystem configured for generating optical based output for a specimen by directing light to and detecting light from the specimen. The system also includes an electron beam based subsystem configured for generating electron beam based output for the specimen by directing electrons to and detecting electrons from the specimen. In addition, the system includes one or more computer subsystems configured for receiving the optical based output and the electron beam based output generated for the specimen. The one or more computer subsystems include one or more virtual systems configured for performing one or more functions using at least some of the optical based output and the electron beam based output generated for the specimen. The one or more virtual systems are not capable of having the specimen disposed therein. The system further includes one or more components executed by the one or more computer subsystems. The one or more components include one or more models configured for performing one or more simulations for the specimen. The one or more computer subsystems are configured for detecting defects on the specimen based on at least two of the optical based output, the electron beam based output, results of the one or more functions, and results of the one or more simulations. Each of the embodiments of the system described above may be further configured as described further herein.

An additional embodiment relates to a computer-implemented method for detecting defects on a specimen. The method includes generating optical based output for a specimen by directing light to and detecting light from the specimen. The method also includes generating electron beam based output for the specimen by directing electrons to and detecting electrons from the specimen. In addition, the method includes receiving the optical based output and the electron beam based output generated for the specimen with one or more computer systems. The one or more computer systems include one or more virtual systems configured for performing one or more functions using at least some of the optical based output and the electron beam based output generated for the specimen. The one or more virtual systems are not capable of having the specimen disposed therein. The one or more components are executed by the one or more computer systems. The one or more components include one or more models configured for performing one or more simulations for the specimen. The method further includes detecting defects on the specimen based on at least two of the optical based output, the electron beam based output, results of the one or more functions, and results of the one or more simulations.

Each of the steps of the method described above may be further performed as described further herein. In addition, the embodiment of the method described above may include any other step(s) of any other method(s) described herein. Furthermore, the method described above may be performed by any of the systems described herein.

Another embodiment relates to a non-transitory computer-readable medium storing program instructions executable on one or more computer systems for performing a computer-implemented method for detecting defects on a specimen. The computer-implemented method includes the steps described above. The computer-readable medium may be further configured as described herein. The steps of the computer-implemented method may be performed as described further herein. In addition, the computer-implemented method for which the program instructions are executable may include any other step(s) of any other method(s) described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
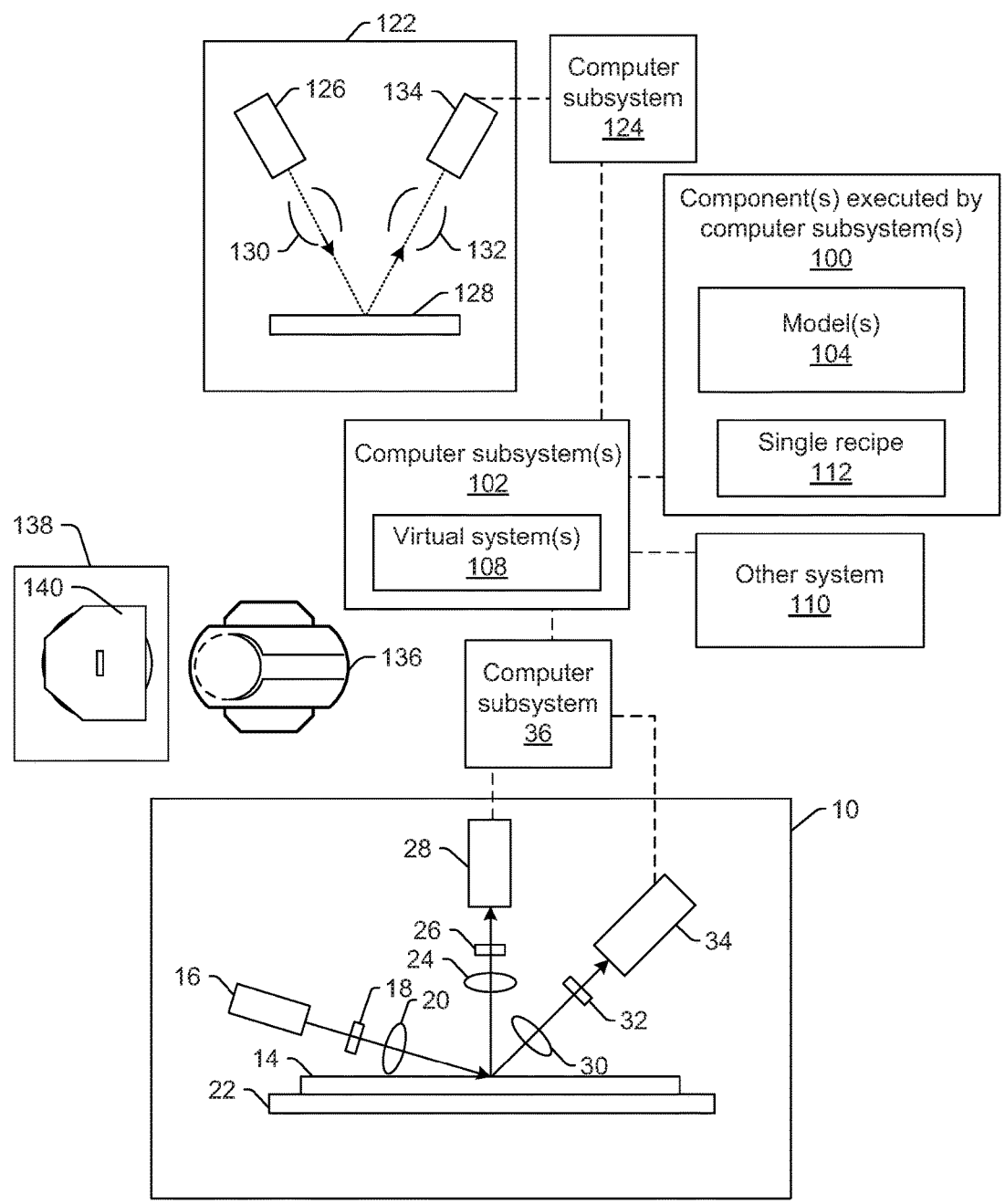
FIG. 1 is a schematic diagram illustrating one embodiment of a system configured to detect defects on a specimen.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The terms "design," "design data," and "design information" as used interchangeably herein generally refer to the physical design (layout) of an IC and data derived from the physical design through complex simulation or simple geometric and Boolean operations. In addition, an image of a reticle acquired by a reticle inspection system and/or derivatives thereof can be used as a "proxy" or "proxies" for the design. Such a reticle image or a derivative thereof can serve as a substitute for the design layout in any embodiments described herein that use a design. The design may include any other design data or design data proxies described in commonly owned U.S. Pat. No. 7,570,796 issued on Aug. 4, 2009 to Zafar et al. and U.S. Pat. No. 7,676,077 issued on Mar. 9, 2010 to Kulkarni et al., both of which are incorporated by reference as if fully set forth herein. In addition, the design data can be standard cell library data, integrated layout data, design data for one or more layers, derivatives of the design data, and full or partial chip design data.

In addition, the "design," "design data," and "design information" described herein refers to information and data that is generated by semiconductor device designers in a design process and is therefore available for use in the embodiments described herein well in advance of printing of the design on any physical specimens such as reticles and wafers.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a system configured to detect defects on a specimen. The embodiments described herein are generally configured for discovering, monitoring, and verifying defect events in the range of greater than 5 nm in size on 100 million to 1000 million locations on a 300 mm logic wafer in 8 to 16 hours. The embodiments described herein can be tuned and/or optimized for lithography and process induced systematic defects, but are generally applicable as enhancements beyond conventional optical inspection tool capability. The embodiments also may be configured as generalized patch based hybrid inspectors for identifying and classifying design and process systematic defects in a semiconductor manufacturing process using a network of deep learning systems that combines optical, scanning electron microscope (SEM) and design patches. As described further herein, key concepts and principles are provided that enable designing, building, and delivering a systems solution that enables users to discover, monitor, and verify lithography and process induced systematic events in the range of greater than 5 nm in size at 100 to 1000 million locations on a 300 mm logic wafer in 8 to 16 hours. The embodiments described herein are in some sense evolutionary, building on earlier ideas of automatic defect classification (ADC), fusion, die-to-database inspection, central compute and storage (CCS), and volumetric inspection, but also can leverage some new understanding of deep learning and exploiting test wafers such as PWQ wafers.

One embodiment of such a system is shown in FIG. 1. The system includes optical based subsystem 10. In general, the optical based subsystem is configured for generating optical based output for a specimen by directing light to (or scanning light over) and detecting light from the specimen. In one embodiment, the specimen includes a wafer. The wafer may include any wafer known in the art. In another embodiment, the specimen includes a reticle. The reticle may include any reticle known in the art.

In the embodiment of the system shown in FIG. 1, optical based subsystem 10 includes an illumination subsystem configured to direct light to specimen 14. The illumination subsystem includes at least one light source. For example, as shown in FIG. 1, the illumination subsystem includes light source 16. In one embodiment, the illumination subsystem is configured to direct the light to the specimen at one or more angles of incidence, which may include one or more oblique angles and/or one or more normal angles. For example, as shown in FIG. 1, light from light source 16 is directed through optical element 18 and then lens 20 to specimen 14 at an oblique angle of incidence. The oblique angle of incidence may include any suitable oblique angle of incidence, which may vary depending on, for instance, characteristics of the specimen.

The optical based subsystem may be configured to direct the light to the specimen at different angles of incidence at different times. For example, the optical based subsystem may be configured to alter one or more characteristics of one or more elements of the illumination subsystem such that the light can be directed to the specimen at an angle of incidence that is different than that shown in FIG. 1. In one such example, the optical based subsystem may be configured to move light source 16, optical element 18, and lens 20 such that the light is directed to the specimen at a different oblique angle of incidence or a normal (or near normal) angle of incidence.

In some instances, the optical based subsystem may be configured to direct light to the specimen at more than one angle of incidence at the same time. For example, the illumination subsystem may include more than one illumination channel, one of the illumination channels may include light source 16, optical element 18, and lens 20 as shown in FIG. 1 and another of the illumination channels (not shown) may include similar elements, which may be configured differently or the same, or may include at least a light source and possibly one or more other components such as those described further herein. If such light is directed to the specimen at the same time as the other light, one or more characteristics (e.g., wavelength, polarization, etc.) of the light directed to the specimen at different angles of incidence may be different such that light resulting from illumination of the specimen at the different angles of incidence can be discriminated from each other at the detector(s).

In another instance, the illumination subsystem may include only one light source (e.g., source 16 shown in FIG. 1) and light from the light source may be separated into different optical paths (e.g., based on wavelength, polarization, etc.) by one or more optical elements (not shown) of the illumination subsystem. Light in each of the different optical paths may then be directed to the specimen. Multiple illumination channels may be configured to direct light to the specimen at the same time or at different times (e.g., when different illumination channels are used to sequentially illuminate the specimen). In another instance, the same illumination channel may be configured to direct light to the specimen with different characteristics at different times. For example, in some instances, optical element 18 may be configured as a spectral filter and the properties of the spectral filter can be changed in a variety of different ways (e.g., by swapping out the spectral filter) such that different wavelengths of light can be directed to the specimen at different times. The illumination subsystem may have any other suitable configuration known in the art for directing the light having different or the same characteristics to the specimen at different or the same angles of incidence sequentially or simultaneously.

In one embodiment, light source 16 may include a broadband plasma (BBP) source. In this manner, the light generated by the light source and directed to the specimen may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source may also include a polychromatic light source that generates light at multiple discrete wavelengths or wavebands.

Light from optical element 18 may be focused onto specimen 14 by lens 20. Although lens 20 is shown in FIG. 1 as a single refractive optical element, it is to be understood that, in practice, lens 20 may include a number of refractive and/or reflective optical elements that in combination focus the light from the optical element to the specimen. The illumination subsystem shown in FIG. 1 and described herein may include any other suitable optical elements (not shown). Examples of such optical elements include, hut are not limited to, polarizing component(s), spectral filter(s), spatial filter(s), reflective optical element(s), apodizer(s), beam splitter(s), aperture(s), and the like, which may include any such suitable optical elements known in the art. In addition, the optical based subsystem may be configured to alter one or more of the elements of the illumination subsystem based on the type of illumination to be used for generating the optical based output.

The optical based subsystem may also include a scanning subsystem configured to cause the light to be scanned over the specimen. For example, the optical based subsystem may include stage 22 on which specimen 14 is disposed during optical based output generation. The scanning subsystem may include any suitable mechanical and/or robotic assembly (that includes stage 22) that can be configured to move the specimen such that the light can be scanned over the specimen. In addition, or alternatively, the optical based subsystem may be configured such that one or more optical elements of the optical based subsystem perform some scanning of the light over the specimen. The light may be scanned over the specimen in any suitable fashion such as in a serpentine-like path or in a spiral path.

The optical based subsystem further includes one or more detection channels. At least one of the one or more detection channels includes a detector configured to detect light from the specimen due to illumination of the specimen by the subsystem and to generate output responsive to the detected light. For example, the optical based subsystem shown in FIG. 1 includes two detection channels, one formed by collector 24, element 26, and detector 28 and another formed by collector 30, element 32, and detector 34. As shown in FIG. 1, the two detection channels are configured to collect and detect light at different angles of collection. In some instances, both detection channels are configured to detect scattered light, and the detection channels are configured to detect tight that is scattered at different angles from the specimen. However, one or more of the detection channels may be configured to detect another type of light from the specimen (e.g., reflected light).

As further shown in FIG. 1, both detection channels are shown positioned in the plane of the paper and the illumination subsystem is also shown positioned in the plane of the paper. Therefore, in this embodiment, both detection channels are positioned in (e.g., centered in) the plane of incidence. However, one or more of the detection channels may be positioned out of the plane of incidence. For example, the detection channel formed by collector 30, element 32, and detector 34 may be configured to collect and detect light, that is scattered out of the plane of incidence. Therefore, such a detection channel may be commonly referred to as a "side" channel, and such a side channel may be centered in a plane that is substantially perpendicular to the plane of incidence.

Although FIG. 1 shows an embodiment of the optical based subsystem that includes two detection channels, the optical based subsystem may include a different number of detection channels (e.g., only one detection channel or two or more detection channels). In one such instance, the detection channel formed by collector 30, element 32, and detector 34 may form one side channel as described above, and the optical based subsystem may include an additional detection channel (not shown) formed as another side channel that is positioned on the opposite side of the plane of incidence. Therefore, the optical based subsystem may include the detection channel that includes collector 24, element 26, and detector 28 and that is centered in the plane of incidence and configured to collect and detect light at scattering angle(s) that are at or close to normal to the specimen surface. This detection channel may therefore be commonly referred to as a "top" channel, and the optical based subsystem may also include two or more side channels configured as described above. As such, the optical based subsystem may include at least three channels (i.e., one top channel and two side channels), and each of the at least three channels has its own collector, each of which is configured to collect light at different scattering angles than each of the other collectors.

As described further above, each of the detection channels included in the optical based subsystem may be configured to detect scattered light. Therefore, the optical based subsystem shown in FIG. 1 may be configured for dark field (DF) output generation for specimens. However, the optical based subsystem may also or alternatively include detection channel(s) that are configured for bright field (BF) output generation for specimens. In other words, the optical based subsystem may include at least one detection channel that is configured to detect light specularly reflected from the specimen. Therefore, the optical based subsystems described herein may be configured for only DF, only BF, or both DF and BF imaging. Although each of the collectors are shown in FIG. 1 as single refractive optical elements, it is to be understood that each of the collectors may include one or more refractive optical elements(s) and/or one or more reflective optical element(s).

The one or more detection channels may include any suitable detectors known in the art. For example, the detectors may include photo-multiplier tubes (PMTs), charge coupled devices (CCDs), time delay integration (TDI) cameras, and any other suitable detectors known in the art. The detectors may also include non-imaging detectors or imaging detectors. In this manner, if the detectors are non-imaging detectors, each of the detectors may be configured to detect certain characteristics of the scattered light such as intensity but may not be configured to detect such characteristics as a function of position within the imaging plane. As such, the output that is generated by each of the detectors included in each of the detection channels of the optical based subsystem may be signals or data, but not image signals or image data. In such instances, a computer subsystem such as computer subsystem 36 may be configured to generate images of the specimen from the non-imaging output of the detectors. However, in other instances, the detectors may be configured as imaging detectors that are configured to generate imaging signals or image data. Therefore, the optical based subsystem may be configured to generate optical images or other optical based output described herein in a number of ways.

It is noted that FIG. 1 is provided herein to generally illustrate a configuration of an optical based subsystem that may be included in the system embodiments described herein or that may generate optical based output that is used by the system embodiments described herein. Obviously, the optical based subsystem configuration described herein may be altered to optimize the performance of the optical based subsystem as is normally performed when designing a commercial system. In addition, the systems described herein may be implemented using an existing system (e.g., by adding functionality described herein to an existing system) such as the 29xx/39xx and Puma 9xxx series of tools that are commercially available from KLA-Tencor, Milpitas, Calif. For some such systems, the embodiments described herein may be provided as optional functionality of the system (e.g., in addition to other functionality of the system). Alternatively, the optical based subsystem described herein may be designed "from scratch" to provide a completely new optical based subsystem.

Computer subsystem 36 coupled to the optical based subsystem may be coupled to the detectors of the optical based subsystem in any suitable manner (e.g., via one or more transmission media, which may include "wired" and/or "wireless" transmission media) such that the computer subsystem can receive the output generated by the detectors for the specimen. Computer subsystem 36 may be configured to perform a number of functions described further herein using the output of the detectors.

The computer subsystems shown in FIG. 1 (as well as other computer subsystems described herein) may also be referred to herein as computer system(s). Each of the computer subsystem(s) or system(s) described herein may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer subsystem(s) or system(s) may also include any suitable processor known in the art such as a parallel processor. In addition, the computer subsystem(s) or system(s) may include a computer platform with high speed processing and software, either as a standalone or a networked tool.

If the system includes more than one computer subsystem, then the different computer subsystems may be coupled to each other such that images, data, information, instructions, etc. can be sent between the computer subsystems as described further herein. For example, computer subsystem 36 may be coupled to computer subsystem(s) 102 as shown by the dashed line in FIG. 1 by any suitable transmission media, which may include any suitable wired and/or wireless transmission media known in the art. Two or more of such computer subsystems may also be effectively coupled by a shared computer-readable storage medium (not shown).

The system also includes an electron beam based subsystem configured for generating electron beam based output for the specimen by directing electrons to (or scanning electrons over) and detecting electrons from the specimen. In one such embodiment shown in FIG. 1, the electron beam based subsystem includes electron column 122, which may be coupled to computer subsystem 124.

As also shown in FIG. 1, the electron column includes electron beam source 126 configured to generate electrons that are focused to specimen 128 by one or more elements 130. The electron beam source may include, for example, a cathode source or emitter tip, and one or more elements 130 may include, for example, a gun lens, an anode, a beam limiting aperture, a gate valve, a beam current selection aperture, an objective lens, and a scanning subsystem, all of which may include any such suitable elements known in the art.

Electrons returned from the specimen (e.g., secondary electrons) may be focused by one or more elements 132 to detector 134. One or more elements 132 may include, for example, a scanning subsystem, which may be the same scanning subsystem included in element(s) 130.

The electron column may include any other suitable elements known in the art. In addition, the electron column may be further configured as described in U.S. Pat. No. 8,664,594 issued Apr. 4, 2014 to Jiang et al., U.S. Pat. No. 8,692,204 issued Apr. 8, 2014 to Kojima et al., U.S. Pat. No. 8,698,093 issued Apr. 15, 2014 to Gubbens et al., and U.S. Pat. No. 8,716,662 issued May 6, 2014 to MacDonald et al., which are incorporated by reference as if fully set forth herein.

Although the electron column is shown in FIG. 1 as being configured such that the electrons are directed to the specimen at an oblique angle of incidence and are scattered from the specimen at another oblique angle, it is to be understood that the electron beam may be directed to and scattered from the specimen at any suitable angles. In addition, the electron beam based subsystem may be configured to use multiple modes to generate electron beam based output for the specimen as described further herein (e.g., with different illumination angles, collection angles, etc.). The multiple modes of the electron beam based subsystem may be different in any output generation parameters of the electron beam based subsystem.

Computer subsystem 124 may be coupled to detector 134 as described above. The detector may detect electrons returned from the surface of the specimen thereby forming electron beam output anchor images of the specimen. The electron beam output anchor images may include any suitable electron beam output and/or images. Computer subsystem 124 may be configured to perform one or more functions described further herein for the specimen using output generated by detector 134. Computer subsystem 124 may be configured to perform any additional step(s) described herein.

It is noted that FIG. 1 is provided herein to generally illustrate a configuration of an electron beam based subsystem that may be included in the embodiments described herein. As with the optical based subsystem described above, the electron beam based subsystem configuration described herein may be altered to optimize the performance of the electron beam based subsystem as is normally performed when designing a commercial electron beam based subsystem. In addition, the systems described herein may be implemented using an existing system (e.g., by adding functionality described herein to an existing system) such as the eSxxx and eDR-xxxx series of tools that are commercially available from KLA-Tencor. For some such systems, the embodiments described herein may be provided as optional functionality of the system (e.g., in addition to other functionality of the system). Alternatively, the system described herein may be designed "from scratch" to provide a completely new system.

The systems described herein may also include one or more additional subsystems configured to generate other output for the specimen such as an ion beam-based subsystem. Such a subsystem may be configured as shown in FIG. 1 with respect to the electron beam based subsystem except that the electron beam source may be replaced with any suitable ion beam source known in the art. In addition, the subsystem may be any other suitable ion beam-based subsystem such as those included in commercially available focused ion beam (FIB) systems, helium ion microscopy (HIM) systems, and secondary ion mass spectroscopy (SIMS) systems.

The system also includes one or more computer subsystems, e.g., computer subsystem(s) 102 shown in FIG. 1, that are configured for receiving the optical based output and the electron beam based output generated for the specimen. For example, as shown in FIG. 1, computer subsystem(s) 102 may be coupled to computer subsystem 36 and computer subsystem 124 such that computer subsystem(s) can receive the optical based output generated by detectors 28 and 34 and electron beam based output generated by detector 134. Although the computer subsystem(s) may receive the optical based output and the electron beam based output from other computer subsystems coupled to the optical and electron beam based subsystems, the computer subsystem(s) may be configured to receive the optical and electron beam based output directly from the detectors that generated the output (e.g., if computer subsystem(s) 102 are coupled directly to the detectors shown in FIG. 1).

As noted above, the optical and electron beam based subsystems may be configured for directing energy (e.g., light, electrons) to and/or scanning energy over a physical version of the specimen thereby generating actual output and/or images for the physical version of the specimen. In this manner, the optical and electron beam based subsystems may be configured as "actual" subsystems, rather than "virtual" systems. Computer subsystem(s) 102 shown in FIG. 1, however, include one or more "virtual" systems 108 that are configured for performing one or more functions using at least some of the optical based output and the electron beam based output generated for the specimen, which may include any of the one or more functions described further herein.

The virtual system(s) provide mass image storage and retrieval with functionally random access conditional retrieval capability. The mass storage infrastructure provided by such virtual system(s) enables the virtual multi-channel aspect of the embodiments volumetric, hyperspectral inspection) described further herein. In addition, a deep learning based virtual multi-channel patch processor can be configured for performing inspection operations on the sample patches (e.g., output generated for different focal planes, spectrums, apertures, etc. and recorded serially can be treated as a single data set). The model(s) described herein, possibly operating on image data stored in the virtual system(s), can also provide another image acquisition data source for a multi-channel virtual system. In other words, results of the model(s) described herein may be considered another channel of information for a multi-channel inspection or other process described herein.

The one or more virtual systems are not capable of having the specimen disposed therein. In particular, the virtual system(s) are not part of optical based subsystem 10 or electron beam based subsystem 122 and do not have any capability for handling the physical version of the specimen. In other words, in a system configured as a virtual system, the output of its one or more "detectors" may be output that was previously generated by one or more detectors of an actual system and that is stored in the virtual system, and during the "imaging and/or scanning," the virtual system may replay the stored output as though the specimen is being imaged and/or scanned. In this manner, imaging and/or scanning the specimen with a virtual system may appear to be the same as though a physical specimen is being imaged and/or scanned with an actual system, while, in reality, the "imaging and/or scanning" involves simply replaying output for the specimen in the same manner as the specimen may be imaged and/or scanned.

Systems and methods configured as "virtual" inspection systems are described in commonly assigned U.S. Pat. No. 8,126,255 issued on Feb. 28, 2012 to Bhaskar et al. and U.S. Pat. No. 9,222,895 issued on Dec. 29, 2015 to Duffy et al., both of which are incorporated by reference as if fully set forth herein. The embodiments described herein may be further configured as described in these patents. For example, the one or more computer subsystems described herein may be further configured as described in these patents. In addition, configuring the one or more virtual systems as a CCS system may be performed as described in the above-referenced patent to Duffy. The persistent storage mechanisms described herein can have distributed computing and storage such as the CCS architecture, but the embodiments described herein are not limited to that architecture.

As further noted above, the optical based subsystem may be configured to generate output for the specimen with multiple modes. In this manner, in some embodiments, the optical based output includes output generated by the optical based subsystem with two or more different values of a parameter of the optical based subsystem. In general, a "mode" can be defined by the values of parameters of the optical based subsystem used for generating output and/or images for a specimen. Therefore, modes that are different may be different in the values for at least one of the optical parameters of the subsystem. For example, in one embodiment of an optical based subsystem, at least one of the multiple modes uses at least one wavelength of the light for illumination that is different from at least one wavelength of the light for illumination used for at least one other of the multiple modes. The modes may be different in the illumination wavelength as described further herein (e.g., by using different light sources, different spectral filters, etc.) for different modes. In another embodiment, at least one of the multiple modes uses an illumination channel of the optical based subsystem that is different from an illumination channel of the optical based subsystem used for at least one other of the multiple modes. For example, as noted above, the optical based subsystem may include more than one illumination channel. As such, different illumination channels may be used for different modes.

In a similar manner, the electron beam based output may include output generated by the electron beam based subsystem with two or more different values of a parameter of the electron beam based subsystem. For example, the electron beam subsystem may be configured to generate output for the specimen with multiple modes. The multiple modes can be defined by the values of parameters of the electron beam based subsystem used for generating output and/or images for a specimen. Therefore, modes that are different may be different in the values for at least one of the electron beam parameters of the subsystem. For example, in one embodiment of an electron beam based subsystem, at least one of the multiple modes uses at least one angle of incidence for illumination that is different from at least one angle of incidence of the illumination used for at least one other of the multiple modes.

The system includes one or more components executed by the one or more computer subsystems, and the one or more components include one or more models configured for performing one or more simulations for the specimen. For example, the system includes component(s) 100 executed by computer subsystem(s) 102. Component(s) 100 include model(s) 104. The model(s) may include a variety of model(s) described herein.

In one embodiment, the one or more models include one or more deep learning based models. Generally speaking, "deep learning" (also known as deep structured learning, hierarchical learning or deep machine learning) is a branch of machine learning based on a set of algorithms that attempt to model high level abstractions in data. In a simple case, there may be two sets of neurons: ones that receive an input signal and ones that send an output signal. When the input layer receives an input, it passes on a modified version of the input to the next layer. In a deep network, there are many layers between the input and output (and the layers are not made of neurons but it can help to think of it that way), allowing the algorithm to use multiple processing layers, composed of multiple linear and non-linear transformations.

Deep learning is part of a broader family of machine learning methods based on learning representations of data. An observation (e.g., an image) can be represented in many ways such as a vector of intensity values per pixel, or in a more abstract way as a set of edges, regions of particular shape, etc. Some representations are better than others at simplifying the learning task (e.g., face recognition or facial expression recognition). One of the promises of deep learning is replacing handcrafted features with efficient algorithms for unsupervised or semi-supervised feature learning and hierarchical feature extraction.

Research in this area attempts to make better representations and create models to learn these representations from large-scale unlabeled data. Some of the representations are inspired by advances in neuroscience and are loosely based on interpretation of information processing and communication patterns in a nervous system, such as neural coding which attempts to define a relationship between various stimuli and associated neuronal responses in the brain.

Various deep learning architectures such as deep neural networks, convolutional deep neural networks, deep belief networks and recurrent neural networks have been applied to fields like computer vision, automatic speech recognition, natural language processing, audio recognition and bioinformatics where they have been shown to produce state-of-the-art results on various tasks.

In another embodiment, the one or more models include one or more machine learning based models. Machine learning can be generally defined as a type of artificial intelligence (AI) that provides computers with the ability to learn without being explicitly programmed. Machine learning focuses on the development of computer programs that can teach themselves to grow and change when exposed to new data. In other words, machine learning can be defined as the subfield of computer science that "gives computers the ability to learn without being explicitly programmed." Machine learning explores the study and construction of algorithms that can learn from and make predictions on data—such algorithms overcome following strictly static program instructions by making data driven predictions or decisions, through building a model from sample inputs.

The machine learning models described herein may be further configured as described in "Introduction to Statistical Machine Learning," by Sugiyama, Morgan Kaufmann, 2016, 534 pages; "Discriminative, Generative, and Imitative Learning," Jebara, MIT Thesis, 2002, 212 pages; and "Principles of Data Mining (Adaptive Computation and Machine Learning)," Hand et al., MIT Press, 2001, 578 pages; which are incorporated by reference as if fully set forth herein. The embodiments described herein may be further configured as described in these references.

The one or more computer subsystems are also configured for detecting defects on the specimen based on at least two of the optical based output, the electron beam based output, results of the one or more functions performed by the one or more virtual systems, and results of the one or more simulations performed by the one or more models. For example, as described further herein, the computer subsystem(s) may be configured for performing a kind of die-to-database inspection on both electron beam based output and optical based output generated for a specimen. The defect detection described herein may be performed at any stage in the processing of the specimen (e.g., any stage in wafer manufacturing) to determine the state of the specimen with respect to any type of defects that may be present on the specimen (e.g., yield relevant defects).

The embodiments described herein, therefore, are essentially a hybrid inspector that is a system of systems and includes algorithms and/or methods for fusing data from an optical based subsystem (e.g., an optical inspector) and an electron beam based subsystem (e.g., a SEM scanning inspector or review system) for the purpose of detecting defects. The resulting detection capability is not fundamentally limited (i.e., the system should also be better at detecting other spatially random defect types relative to a conventional system).

Although the embodiments described herein may be somewhat more complex (operationally and computationally) than inspection systems that include only a single type of output generation hardware (e.g., imaging hardware), the embodiments described herein provide a net sensitivity improvement for defect detection, and the setup of the embodiments described herein can be biased to detection of systematic defects. "Systematic" defects can be generally defined in the art as defects that are caused by an interaction between a process performed on the specimen and a design formed on the specimen. Therefore, "systematic" defects may be formed at multiple, repeating locations across a specimen.

In another embodiment, detecting the defects is also performed based on design information for the specimen in combination with at least two of the optical based output, the electron beam based output, the results of the one or more functions, and the results of the one or more simulations. For example, the embodiments described herein may be configured for fusing data from three or more sources (e.g., design, optical, and electron beam) for defect detection. In one such embodiment, the design information may be used as described further herein to generate a reference for the specimen that is used with one of the optical based output or the electron beam based output (different references may be generated for different output). In addition, or alternatively, the design information may be used to determine one or more parameters of the defect detection that is performed with the at least two of the optical based output, the electron beam based output, the results of the one or more functions, and the results of the one or more simulations. The one or more parameters of defect detection determined based on the design may include, for example, care areas (areas where defect detection is performed), critical areas (areas where higher sensitivity inspection is to be performed compared to non-critical areas), etc. The design information (or information derived from the design information such as a context map) may also or alternatively be used in a variety of other ways described further herein.

In some embodiments, detecting the defects includes comparing the optical based output to a first reference and comparing the electron beam based output to a second reference. Detecting the defects as described above may be effectively performed with a kind of die-to-database inspection on both electron beam and optical images. Since the optical based output and the electron beam based output will have substantially different characteristics (e.g., resolution, contrast, etc.), different references may be used for detecting defects with the different output. In some such embodiments, although the defect detection may include two separate comparisons, the separate comparison steps may be unlike those performed for inspection and then defect review in that the decisions about whether or not there are defects present at any locations on the specimen may not be made until after both comparisons are performed. In this manner, the results of both comparisons steps may be used to detect defects on the specimen rather than using one comparison to detect defects and another comparison to confirm detected defects. In addition, both comparisons may be performed for locations on the specimen at which it is unknown, at the time of the comparisons, if defects are present at the locations. In other words, both comparisons may be performed for inspection rather than inspection and then review.

In one embodiment, the virtual system(s) are configured for generating a reference for the specimen based on design information for the specimen, and the reference is used for detecting the defects on the specimen. The virtual system(s) may also be configured for generating both of the references described above. The virtual system(s) may be configured for generating the reference as described further herein (e.g., using a generative model) or in any other manner known in the art.

In this manner, the defect detection described herein may be die-to-database type inspection in which the design acts as a kind of connection between different types of information and/or output. The design can also provide constraints and help learn the correct transformational relationship between optical and electron beam modalities. For example, the optical based output generated at one location on the wafer can be correlated with the electron beam based output generated at the same one location such that the two outputs may be used together to detect defects on the specimen.

In one such embodiment, the system may leverage machine learning for die-to-database inspection algorithms and/or as a ground truth trainer for an optical based subsystem. For example, the ground truth here may be a reference image. Using model(s) trained to convert an image in one domain to an image in another domain, high confidence sources of images (e.g., rendered from a design layout or an electron beam based image) can be converted into what it should look like on the optical based subsystem and that may be used as a reference image thereby essentially providing a way to implement die-to-database inspection. In this manner, the embodiments described herein may highly leverage the relationship between optical and SEM images. The embodiments may produce a union of results from the optical inspection "virtual channels" (e.g., 100 to 1000 million optical sites) as well as the electron beam based subsystem (e.g., up to 500,000 sites) thereby enabling the optical images to be inspected or verified at electron beam accuracy.

The embodiments described herein may also be configured to automatically leverage any model(s) for electron beam based/ground truth classification while the optical based subsystem is being re-tuned. For example, the concurrency of processing substantially high volumes of optical data in the ways described herein may be leveraged while also collecting "ground truth" (e.g., high resolution and high confidence) data from an electron beam based subsystem (image acquisition plus classification or detection). The classification with deep learning is essentially "recognition" where one example can be taught and then used to find other instances of the same example in image data.

The embodiments described herein can, therefore, be configured for die-to-database electron beam inspection. For example, as described above, the core technical approach is in a sense agnostic to die-to-database. The electron beam based die-to-database applications can be broken down into different categories. One category is critical point inspection (CPI) die-to-database. CPI inspection is a type of inspection that is performed by grabbing output at only discrete locations (e.g., known critical points) on a specimen. In this type of inspection, die-to-database and single image detection are important for 2× gain in throughput. Another category is full die-to-database (i.e., die-to-database performed for a full die or a full specimen), which can be used to find a variety of issues including optical proximity correction (OPC) systematic defects, hard repeating defects, and random defects. "Hard repeating defects" can be generally defined as a defect that repeats at every instance of a pattern in a die regardless of process conditions used to print the pattern instances.

In a further embodiment, the virtual system(s) are configured for storing all of the optical based output and the electron beam based output generated for the specimen indefinitely. For example, the virtual system(s) may be configured as a persistent storage mechanism that is capable of storing stacks of optical images for whole wafers or a subset of images (e.g., 100-1000 million patches) per wafer. In an additional example, the virtual system(s) may store optical and electron beam images for a prescribed subset of a wafer.

In another embodiment, the virtual system(s) are configured for generating information for the specimen without using the optical based output and the electron beam based output generated for the specimen and for storing the information generated by the one or more virtual systems in the one or more virtual systems. For example, as described further herein, the virtual system(s) may be configured to generate a reference for the specimen from design information for the specimen (and without optical based output and electron beam based output generated for the specimen). Other types of information that may be generated by the virtual system(s) include a context map of the specimen generated from the design information. The context map may indicate different types of patterns and/or areas on the specimen and possibly different parameters that are to be used for defect detection of the different types of areas and/or patterns. The information may also include information from another system such as that described further herein.

In some embodiments, the computer subsystem(s) are configured for receiving information for the specimen generated by another system, the one or more virtual systems are configured for storing the information, and detecting the defects is performed based on the stored information in combination with the at least two of the optical based output, the electron beam based output, the results of the one or more functions, and the results of the one or more simulations. For example, as shown in FIG. 1, computer subsystem(s) 102 may be coupled to other system 110 such that the computer subsystem(s) can receive information from the other system. The other system may include a variety of other systems such as an EDA tool, another computer system, which may be configured for a variety of different capabilities, a semiconductor fabrication tool, another inspection system, another quality control type system, etc. The information for the specimen may include a variety of information for the specimen such as information related to the design for the specimen, one or more fabrication processes performed on the specimen, one or more inspection, measurement, or other quality control processes performed on the specimen or another specimen of the same or different type, results of simulations generated for the specimen, information generated for the specimen from another source, etc. In this manner, the embodiments described herein can access and acquire a variety of prior information and reference data that can be used in a number of different steps described herein.

In one such example, the information from the other system may include information for critical patterns in a design for the specimen, which may be included in a database of such information. This information may be generated in a variety of ways such as by a process window qualification (PWQ) method, a design of experiments (DOE) that is performed empirically, simulations, volume diagnostics (VD), pattern fidelity analysis (PFA), etc. Such information may also include reticle PWQ analysis.

PWQ methods may be performed as described in U.S. Pat. No. 6,902,855 to Peterson et al. issued on Jun. 7, 2005, U.S. Pat. No. 7,418,124 to Peterson et al. issued on Aug. 26, 2008, U.S. Pat. No. 7,729,529 to Wu et al. issued on Jun. 1, 2010, U.S. Pat. No. 7,769,225 to Kekare et al. issued on Aug. 3, 2010, U.S. Pat. No. 8,041,106 to Pak et al. issued on Oct. 18, 2011, U.S. Pat. No. 8,111,900 to Wu et al. issued on Feb. 7, 2012, and U.S. Pat. No. 8,213,704 to Peterson et al. issued on Jul. 3, 2012, which are incorporated by reference as if fully set forth herein. The embodiments described herein may include any step(s) of any method(s) described in these patents and may be further configured as described in these patents. A PWQ wafer may be printed as described in these patents.

The information from the other system may also be generated by performing a process on the specimen with two or more different values of one or more parameters of the process in a PWQ method designed for overlay margin determination. For example, critical patterns may be identified by performing DOEs such as printing and inspecting overlay-PWQ wafers as a generator of systematic defects. Overlay margin determination may be performed in any suitable manner including as described in the above-referenced patents. Therefore, an overlay-PWQ method may be used to print such dies on a specimen, and examination of the specimen may indicate which patterns are critical. In particular, a standard PWQ process may be performed followed by a first pass inspection, which may be performed using a standard defect detection algorithm. A standard defect review process may then be performed using a known good algorithm for detection. All failed sites may be determined based on results of the first pass inspection and defect review process. Any new patterns of interest (POIs) may then be created for the failed sites.

In an additional such embodiment, the critical patterns may be identified by performing a process with two or more different values of one or more parameters of a process in a focus exposure matrix (FEM) method. For example, one strategy for identifying the critical patterns is to use DOEs such as FEM methods and/or wafers as a generator of systematic defects. FEM methods generally involve printing a number of dies on a wafer at different combinations of focus and exposure parameter values of a lithography process. The different dies can then be inspected in any suitable manner to detect defects in the different dies. That information is then typically used to determine a process window for the focus and exposure of the lithography process. Therefore, a FEM method may be used to print such dies on a specimen, and the critical patterns may be identified on the specimen by an inspection, metrology, etc. process.

Simulations used to identify critical patterns may be performed with an empirically trained process model such as SEMulator 3D, which is commercially available from Coventor, Inc., Cary, N.C. An example of a rigorous lithography simulation model is Prolith, which is commercially available from KLA-Tencor, which can be used in concert with the SEMulator 3D product. However, the simulations may be performed with any suitable model of any of the process(es) involved in producing actual specimens from design data. In this manner, a model may be used to simulate what a specimen on which a design has been formed will look like in specimen space (not necessarily what such a specimen would look like to a system such as an imaging or metrology system). Therefore, the output of the model may represent what the specimens would look like in 2D or 3D space of the specimens.

Volume diagnostics may be performed in any suitable manner. For example, correlating defect locations from a relatively large number of devices, prioritizing those with the highest yield impact, and taking immediate corrective action has potentially enormous cost benefits by enabling faster time to market when new designs are being ramped up in manufacturing. This approach is known as volume diagnostics, and can also be used to help identify the root cause of spurious process excursions, and to make continuous yield improvements which increase long-term manufacturing efficiency.

PFA may be performed as described in U.S. Patent Application Publication No. 2016/0116420 to Duffy et al. published on Apr. 28, 2016, which is incorporated by reference as if fully set forth herein. The embodiments described herein may be further configured as described in this publication.

In another example, the information from the other system may include signals to date generated for the specimen such as measurement, inspection, other yield related analysis, etc. The signals to date may also include results of edge placement error (EPE) analysis and/or predictive EPE (PEPE), which may be performed in any suitable manner known in the art. In this manner, the EPE analysis may include one or more empirical processes and/or one or more simulation processes.

In an additional example, the information from the other system may include design information for the specimen such as product information, design for inspection (DFI) information, target information, and design fusion information. Design fusion is a software development program targeting the transfer of critical design information from fabless customers into the fab for use by tools not owned or operated by the fabless customers. Such critical design information may include, for example, care areas for parts of the layout, timing critical nets, and the like. In some such examples, the other system may include an electron design automation (EDA) tool. In this manner, the embodiments described herein may have an added dimension of leveraging data generated with EDA computer aided design (CAD) tools. The FDA tool may include any suitable commercially available EDA tool.

In a further example, the information from the other system may include standard reference images and/or information for noise sources on the specimen. The standard reference images may be generated in any suitable manner. The information for the noise sources may be generated in any suitable manner. The information from the other system may further include generated images. The generated images may be generated in any suitable manner such as by a model and/or another simulation model.

The specimens described herein may include a variety of different wafers such as nominal instances of the wafers and/or non-nominal instances of the wafers. "Nominal instances" as that term is used herein is generally defined as "instances" of specimens on which no defects are known to be present. For example, the specimen(s) that are nominal may be processed with one or more parameters of one or more processes, used to form a design on the specimen(s), that are known to generate non-defective specimens. In other words, the process(es) used to fabricate the specimen(s) may be known good process(es). In addition, the "nominal instances" of the specimen(s) may include instances (e.g., locations on specimens, whole specimens, etc.) at which no defects have been determined to be present. For example, the nominal instances of the specimen(s) may include locations and/or specimens at which an inspection or other quality control related process (e.g., defect review, metrology, etc.) has not detected any defects.

In contrast, "non-nominal instances" of the specimen(s) as that term is used herein is generally defined as "instances" of the specimen(s) that are "defective" in some manner, either intentionally (via programmed or synthetic defects as described further herein) or unintentionally (via defects discovered on one or more specimens by inspection, defect review, metrology, etc.). In addition, it is noted that a specimen may be "defective" even if no "defects" per se are detected on the specimen. For example, a specimen may be considered "defective" if one or more measurements indicate that one or more characteristics of a design formed on the specimen are outside of a desired range of values for those one or more characteristics.

The specimens may also include product wafers (possibly with design for inspection (DFI) structures formed thereon) and/or characterization vehicles (i.e., electrical test structures). The DFI structures may be configured as described further herein.

Receiving or acquiring the information from the other system may be performed by receiving or acquiring the information from the other system itself. However, receiving and/or acquiring the information from the other system may include acquiring the information generated by the other system from a storage medium (not shown) in which the information has been stored by the other system. The embodiments described herein, however, may also be configured for generating any of the information described above that may be received from the other system. For example, the systems described herein may be configured to generate the information described above by performing one or more processes on actual specimens (e.g., performing one or more fabrication processes on an actual, physical specimen and then performing one or more measurement and/or imaging processes on the actual physical specimen). Therefore, the information described above may be generated using the computer subsystem(s) described herein with one or more other subsystems described herein (e.g., one or more semiconductor fabrication subsystems, one or more imaging subsystems, one or more metrology subsystems, etc.). In another example, the information described above may be generated by the systems described herein, e.g., by performing one or more simulations (with or without using actual, physical specimens). In one such example, the one or more computer subsystems may be configured to use one or more of the model(s) and/or another model to generate the information for the nominal and/or non-nominal instances of the specimen(s).

The embodiments described herein may, therefore, be configured for raw data acquisition that may be performed on some measurement and/or inspection tool and/or sensor (such as the optical based subsystem and/or electron beam based subsystem described herein). The raw data acquisition may also be performed using a virtual multi channel system and/or method. A virtual multi-channel method may include collecting output or image data in different optical or electron beam modes serially for the same location and storing the image data in a virtual system for post-processing, which is performed as though the separate images are one image collected by a multi-channel inspector. Examples of systems and methods that can be used for virtual multi-channel data acquisition are described in U.S. Patent Application Publication No. 2016/0025648 by Duffy et al. published on Jan. 28, 2016, which is incorporated by reference as if fully set forth herein. The embodiments described herein may be further configured as described in this publication. The raw data acquisition may also be performed on product geometry (e.g., patterned features of devices being formed with or on the specimens) and/or metrology targets formed on the specimens. In addition, the raw data acquisition may be performed using on-wafer instrumentation.

The system can use the persistent information described herein (i.e., the information stored in the virtual system(s)) possibly in combination with other persistent information to perform z based inspection, e.g., using data acquired through the stack of materials or layers formed on the specimen. For example, output generated for the specimen at different physical planes (layers in the process) may be stored in the virtual system(s) described herein. This information can then be used to determine a source of a defect detected on the specimen. In other words, the persistently stored information in the virtual system(s) may be used for defect source analysis by considering information (e.g., optical based output and/or electron beam based output) generated for different layers on the specimen. In this manner, the information that is stored in the virtual system(s) may be used to separate defects detected on one layer into defects that are located on that layer and defects that are located on another (e.g., a previous) layer on the specimen. As such, the information can be used to identify defects detected on a layer of a specimen that are actually previous layer nuisance defects (i.e., defects that are present on a different layer and are visible to the subsystem that generated the output used for inspection and yet are not defects that, the user cares about).

In a further embodiment, the specimen includes DFI structures, and the one or more computer subsystems are configured for extracting at least one of the optical based output and the electron beam based output generated for the DFI structures and performing one or more functions based on the extracted output. DFI structures may include programmed defects and/or voltage contrast metrology or defect test structures. In this manner, the DFI structures may essentially be embedded instrumentation. Design considerations for the DFI structures include a set of structures that enable the selection of a range of tool setup conditions that span the setup variable space of the tool (e.g., including programmed defect structures that demonstrate the best signal to noise performance at each of the spectral bands that the tool is capable of, etc.). Design considerations for the DFI structures also include compression of the key optically significant geometry structures into a relatively sparse set of DFI structures suitable for evaluating the spatial variation of both noise (for reference layouts) and signal (for programmed defect structures). The DFI structures may also be used for on-wafer extraction of reference data that can be used as the reference data described further herein. In other words, the system can exploit ground truth information such as that coming from in-die DFI structures (e.g., in dummy fill areas) by tightly coupling algorithms to the predictable presence of structures optimized for generating optical noise and signal data at substantially high spatial resolution.

In some embodiments, detecting the defects includes volumetric inspection. In general, volumetric inspection includes using an inspection tool to collect intensity data sets at a plurality of focus settings from each of a plurality of xy positions of the sample. A polynomial equation having a plurality of coefficients is extracted for each of the xy position's collected intensity data sets as a function of focus setting. Each of the coefficients' set of values for the plurality of xy positions is represented with a corresponding coefficient image plane. A target set of coefficient image planes and a reference set of coefficient image planes are then analyzed to detect defects on the sample. In this manner, a tuple of volumetric images can be transformed into a Fourier spatial domain for the purpose of separating signal from noise. Volumetric inspection may be further performed as described in U.S. Patent Application Publication No. 2016/0209334 by Chen et al. published on Jul. 21, 2016, which is incorporated by reference as if fully set forth herein. The embodiments described herein may be further configured as described in this publication. In the embodiments described herein, the optical based output of the optical based subsystem may include volumetric stacks of optical images (e.g., between 3 to 5 z stacks) to enable a solution to the so called "phase" problem in optical space. The optical system tuple concept can also be extended to include other optical modes besides the z focus images such as different wavelengths and apertures.

The model(s) described herein may have a one-to-many transformation problem. For example, since virtually all optical systems can be modeled as a thin film stack, variations in the film stack along with variations in the wafer topography implies that there is a one-to-many mapping when going from electron beam based output to optical based output. Of course, all these variations could be learned, but they are also the source of noise particularly if they occur locally (e.g., due to local color variations). Customers often have OPC corrections on many structures which lead to different contrast than say on dummy fills or non-corrected layers. There are a myriad of hand crafted algorithms to cope with these but none of them are totally effective.

There are also limitations of comparison based algorithms. For example, prior layer noise and line edge roughness (LER) are like the proverbial "aluminum grain noise" problem in some optical inspectors which is difficult to solve in a practical manner. The reason is simple—at the root of this problem is the die-to-die inspection paradigm, which is very good at finding random events. The convention die-to-database approach of rendering is also substantially challenging. In the end, even if the database is rendered, a comparison algorithm is then used. The word "signal" is often used when what is meant by that are two things a) do you see the event on an electron beam based subsystem?; and b) does the die-to-die comparison method rise above the noise floor? With good reason, attempts are usually made to try to eliminate the "pattern" by subtracting it and hoping the signal sticks out. However, no such thing is done on electron beam based subsystems (even though it can be done) because the resolution is available to make a direct call on the electron beam based output (single images) without having to compare it to a reference.

To overcome the limitations described above, deep learning combined with volumetric inspection is proposed. In particular, it is believed that a deep learning approach is superior particularly when combined with an optical volumetric stack of z images. The latter helps to mitigate the one-to-many mapping problem and to shore up the "signal." For example, the volumetric information captures "phase" information in addition to "intensity" information from the optical based output. In contrast, normal optical based inspection only works from "intensity," which is a cause of ambiguity (the "many" in the "one-to-many" mapping). Therefore, the embodiments described herein can exploit patches of image data taken through focus for the purpose of resolving the many-to-one mapping representation problem between optical (many images can represent) to electron beam (the ground truth).

In another embodiment, detecting the defects includes hyperspectral inspection. For example, the multi-spectrum capability of the optical based subsystems described herein can be used in concert with hyperspectral deep learning analysis techniques. In particular, some of the optical based subsystems described herein (e.g., optical based subsystems that include broadband light sources) have multiple spectral modes, each across only a portion of the EM spectrum. The notion of "hyperspectral" in the context of the embodiments described herein means that output and/or images are collected from a location across some or all of the available portions of the spectrum. In this manner, multiple optical based outputs may be generated for a single location on a specimen (as well as each other location for which output is generated) at different spectral modes, and the inspection of the location may be performed using two or more (or all) of the outputs generated at the different spectral modes.

In a further embodiment, detecting the defects includes multi-mode inspection. For example, the multi-mode inspection may be performed with different focus settings and/or different spectral settings as described further above. However, the multi-mode inspection may also or alternatively be performed with modes that are different in any other parameters of the optical based subsystem and/or electron beam based subsystem that are used to generate the optical based output and/or electron beam based output used for inspection. In particular, a "mode" used to generate optical based output and/or electron beam based output may be defined by the parameters of the optical based subsystem and/or electron beam based subsystem used to generate that output. Therefore, a "mode" may be defined, in the case of an optical based subsystem, by values for parameters such as illumination wavelength(s), illumination polarization(s), illumination angle(s) of incidence, illumination aperture(s), detection wavelength(s), detection polarization(s), detection angle(s), detection aperture(s), etc. Modes of an electron beam based subsystem may be defined in a similar manner based on the electron beam related parameters of that subsystem. When defect detection is performed using multiple modes, multiple outputs may be generated for a single location on a specimen (as well as each other location for which output is generated) at different modes, and the inspection of the location may be performed using two or more (or all) of the outputs generated at the different modes. Such inspection may be performed in any suitable manner known in the art.

In an additional embodiment, the one or more models are configured for classifying the detected defects, and the one or more computer subsystems are configured for sampling the detected defects based on results of the classifying. The sampling may also be performed as a function of any data that is available to the system such as any of the information described herein that may be received from another system. In this manner, the embodiments described herein may be configured for deep learning based sampling. The sampling described herein may be deep learning based in that sampling can be an extension of using deep learning for classification (find all the images of a certain type and sample a given percentage of them). The deep learning based sampling may be also be performed based on the available prior/reference data described further herein as well as information generated by the embodiments described herein. Reference data may include information about pattern weakness (poor resiliency to process variation), design layout information, metrology information (from external sources or in situ).

The results of the sampling may be used to direct any post-processing that may be performed for the specimen. For example, one or more simulations may be performed by the models described herein for the sampled defects. In addition, the post-processing may be performed for patches of design and/or experimentally and/or theoretically generated images for the defects.

The raw data acquisition, sampling, and post-processing described above may be performed in a feedback loop. For example, the results of the post-processing may be used to direct additional raw data acquisition that may be performed for the specimen. The results of the raw data acquisition and/or any functions performed using the acquired raw data may be input to the sampling. The results of the sampling may be used to direct any additional post-processing, which may be used to generate any further raw data acquisition. In this manner, the raw data acquisition, sampling, and post-processing described above may be performed in a signal amplification loop until the process is completed.

In yet another embodiment, the one or more computer subsystems are configured for performing detecting the defects using the one or more models. The model(s) can also be used to replace a range of traditional hand crafted inspection algorithms to provide much more robust detection and monitoring capability. For example, model(s) may be provided with a number of samples (e.g., both defect samples and non-defect samples), and the model(s) may train themselves for defect detection. In contrast, conventional defect detection algorithms and methods require a user to understand all of the inputs that need to be configured in an algorithm based on their understanding of the input and output data they are observing. Such user-based functions are tedious, time consuming, and error prone. In contrast, model(s) appear to be capable and substantially robust (e.g., do not blow up with nuisance detections, for example, whereas this happens quite frequently with conventional defect detection algorithms and methods that are set up manually). Setting up the model(s) for defect detection may be performed based on sufficient samples (both positive and negative) for learning different types of real and augmented events. Such defect detection can complement traditional defect detection algorithm(s) and/or method(s), which can be used as a bootstrapping mechanism for the learning phase (i.e., broadband plasma inspection-based PWQ for optical network training, etc.).

In a further embodiment, the one or more components include a single recipe configured for controlling at least the optical based subsystem and the electron beam based subsystem. For example, as shown in FIG. 1, component(s) 100 may include single recipe 112. The single recipe may be essentially a super-recipe that includes conditional execution and loop triggering. The intent of a single recipe may be to insure self-consistency within the system operation flow (which is more complex than a conventional inspector). The main self-consistency issue in the embodiments described herein may be spatial (e.g., if you want to use images or output collected in multiple modes of an inspector or review SEM, each image or output acquisition has to be performed in the same location). There may also be reusable recipe components that capture the geometric information about the layout of the wafer and die etc. that can be applied throughout the super recipe, which could involve data collection from different tools. Today, this can be done manually. The proposed system may enforce this by considering the collection of recipes in aggregate (a super-recipe), rather than the conventional collection of separate recipes for the inspector, one for the electron beam review tool, etc.

In some embodiments, the computer subsystem(s) are configured for training the one or more models with information for defects detected in a process window qualification (PWQ) method. The PWQ method may be performed as described further herein. For example, a process may be performed on a specimen with the two or more different values of one or more parameters of the process in a PWQ method. In one such example, one strategy for generating the training input is to use DOEs such as PWQ as a generator of systematic defects. The one or more parameters of the process that are varied in the PWQ method may include focus and exposure (e.g., as in a focus-exposure PWQ process). In addition, the PWQ method may be a simulated PWQ method in which simulations may be performed to generate simulated representations of the specimen processed with different values of at least one parameter of the process. The PWQ method may be further performed using actual specimens and/or simulated specimens as described further herein.

In this manner, test specimens that may be used in the embodiments described herein may include process DOE specimen vehicles and simulated process DOEs using software as generators of systematic defects. As an example, the PWQ wafer will not only function as a PWQ vehicle, but also as a source of systematic pattern defects. These generators can be used to train model(s). Other types of specimens and experiments may also be used for the training. For example, PWQ/FEM/overlay PWQ wafers that are usually used to determine process windows may be used in the embodiments described herein as generators of defects to train any class of machine learning systems including, but not limited to, deep learning systems for both optical based subsystems and electron beam based subsystems. In this manner, the PWQ method may be used to generate non-nominal instances of the specimen that can be used to train the deep learning method(s). In other words, the defect mechanisms used to train and optimize the system may be systematic or process systematic defects. In addition, the electron beam based output generated by the electron beam subsystem for the specimen and/or other specimens may be used to establish the ground truth for learning as well as for verification.

In another embodiment, the embodiments described herein may have the capability to perform one or more PWQ related features. For example, the embodiments described herein may be configured for process window discovery (PWD) that outputs a reference database that is usable for hot spot monitoring and metrology. PWD may be performed using after develop inspection (ADI) wafers and after etch inspection (AEI) wafers, associated metrology data, and design. A generative process such as that described further herein may infer an AEI SEM image from an ADI SEM image (and vice versa). The ADI to AEI (or vice versa) image generation input may include critical dimension (CD) metrology data from the source image. In some instances, the model(s) described herein may be configured to learn a relationship between output of the optical and/or electron beam based subsystem and one or more values of a parameter of a process performed on a specimen. In this manner, the model(s) may be configured to infer process conditions (e.g., focus, dose, etc.) from measured attributes.

In one such embodiment, POIs may be identified by PWQ as described further herein. Volumetric inspection may then be performed at nominal modulation on all failing POI sites. The volumetric inspection may be performed as described further herein. A random sample of volumetric optical patches may then be generated for all failing and non-failing sites. The sample may include up to 5×100 million patches. Defect review may then be performed to verify the failed sites. The sample of failed sites that are reviewed may be selected by diversity sampling. Defect review may be performed to verify failed sites identified by volumetric inspection. In addition, defect review may be performed to verify non-failing sites. Results of the defect review (e.g., whether a site identified by the volumetric inspection or the defect review is failing or not failing) can be stored in the virtual system(s) described herein.

The system may then train the model(s). For example, the model(s) may be trained with volumetric patches, electron beam based images, and design clips. All failed sites may be input and an appropriate number of non-failing sites may also be input. The training may be verified on non-training sites. Volumetric inspection performed with deep learning based defect detection may then be performed. For example, deep learning based detection and/or classification can be performed based on volumetric patch image input. Nominal sites may be inspected using volumetric images input to the model(s).

Results of the defect detection may be used to determine if performing model based detection on volumetric images eliminates any gaps between that inspection and electron beam based inspection. The "gaps" may be defined in this instance as defects that are detected by electron beam based inspection but are not detected by optical based inspection. If there are still gaps between that inspection and electron beam based inspection, additional sites may be selected for defect review. The defect review may be performed on the additional sites as described above to identify failed and non-failed sites. That information may be used to retrain the model(s). Additional volumetric images may be generated and input to the re-trained model(s). Results of that inspection may be used to determine if any gaps remain between the inspection and electron beam based inspection. This process may be repeated until it has been determined that no gaps exist between the deep learning based inspection performed using volumetric images and electron beam inspection.

A number of technical considerations may be made when using information from non-nominal instances of the specimen to train the model(s). For example, the non-nominal instances will be, by definition, detected in non-nominal dice. In addition, in the case of SEM inspection, on the non-nominal dice, the defective pixels can be marked using the SEM. The information from the non-nominal instances may also be leveraged with synthetic defects induced in the design CAD. The SW to induce these defects can be automated or semi-automated. Example defect types to induce can include: opens, shorts, protrusions, intrusions, etc. A SEM image can then be generated by using generative model(s), and these "cartoon-like" defects can be converted into realistic looking defects on a SEM image.

In one such example, training the model(s) may also be performed using instances of defects on one or more specimens, and the defects include one or more synthetic defects generated by altering a design for the one or more specimens to create the synthetic detects in the design. "Synthetic" defects as that term is used herein can be generally defined as one or more defects purposefully caused on a specimen, e.g., by manipulation of the design information for the specimen. Therefore, "synthetic" defects may also be referred to as "hypothetical" defects or "programmed" defects. In one such embodiment, for training input generation via introduction of virtual defect events in design/simulation space by using synthetic approaches, CAD design can be used to synthetically generate defects (e.g., opens, shorts, protrusions, line ends, metrology markers, etc.) and then be treated by a deep generative or other model as described further herein (to create realistic defects on training images) and/or be used to print the synthetically generated defects on one or more specimens, which can then be used to generate images of the synthetically generated defects on the specimen(s). In this manner, the embodiments described herein may include a deep generative model combined with a synthetic method of generating defects on EDA/CAD data to produce realistic systematic and random defects on both electron beam based output and optical based output to inject into the training set for use by any machine learning algorithm including, but not limited, deep learning model(s). The CAD work can be automated with a programmable/graphical EDA editor, which may include any suitable EDA software, hardware, system, or method.

Training the model(s) may further be performed using non-nominal instances of the specimen that include instances of defects on one or more specimens, the defects include one or more synthetic defects generated by altering a design for the one or more specimens to create the synthetic defects in the design, the information for the non-nominal instances includes output of another model, and the output of the other model illustrates how the one or more specimens on which the synthetic defects are printed appear in one or more actual images of the specimen generated by an imaging system. For example, an additional capability that can be applied is simulation of the inspector. An example of such a model is WINsim, which is commercially available from KLA-Tencor, and which can rigorously model the response of an inspector using an electromagnetic (EM) wave solver. In this manner, defect behavior for programmed defects can be learned in one model and applied in another. Such simulations may be performed for any other imaging subsystems or systems described herein. In addition, such simulations may be performed using any other suitable software, algorithm(s), method(s), or system(s) known in the art.

In one embodiment, the one or more components include a deep generative model configured to create information for nominal instances of one or more specimens on which a process is performed. For example, deep generative models that learn the joint probability distribution (mean and variance) between the SEM (image of actual wafer) and design (e.g., CAD or a vector representation of intended layout) can be used to generate nominal instances that are used to train the model(s). A generative model may also be used to generate other simulation results described herein for non-nominal instances of the specimen. Once the model(s) are trained for nominal (as intended/non-defective) samples, a training input dataset, which includes defective images or other non-nominal instances described herein, can be used to train the model(s). In addition, model(s) can be pre-trained by using synthetic data that is generated by modifying design data (e.g., CAD or EDA data) used to make semiconductor wafers. Defect artifacts such as opens, shorts, protrusions, intrusions, etc. along with metrology markers such as line end pull backs could be inserted into the CAD and then fed into a generative model trained by a network described in U.S. patent application Ser. No. 15/176,139 to Zhang et al. filed Jun. 7, 2016, and "Semi-supervised Learning with Deep Generative Models," Kingma et al., NIPS 2014, Oct. 31, 2014, pp. 1-9, which are incorporated by reference as if fully set forth herein, to create realistic defects. The embodiments described herein may be further configured as described in these references.

One consideration for the architectural parameters of the embodiments described herein is the notion of how many samples are needed for doing a specific type of deep learning. For example, for electron beam based model(s), about 1K to about 5K electron beam images may be acquired for the purpose of training the electron beam based model(s) for a given layer. The raw numbers may be roughly 100 samples per defect type. Simulation can also be used to augment defects, which can potentially reduce the number closer to 10. Samples may also be acquired for learning the nominal. For optical based model(s), about 10K to about 50K electron beam samples and corresponding optical samples may be acquired for training. Training the optical based model(s) will require an order of magnitude more than the electron beam based model(s) to overcome resolution and noise in the optical based output. There may also be a final sampling from optical to electron beam for verification (i.e., an optical/electron beam sampling ratio). In addition, one or more of the model(s) described herein may be tested after it has been trained by using a subset of data that was not used for training (i.e., one portion of the data is used for training only, and another portion of the data is used for verification only). For example, SEM ADC is capable of about 90% contribution or better. An operator can cope with 1000 to 2000 defects in an 8 hour session for verification. This leads to approximately 20K samples for verification purposes as one lower bound.

In one embodiment, the model(s) include one or more discriminative models. In another embodiment, the model(s) include one or more generative models. For example, learning can feature two types of mechanisms: discriminative learning that can be used to create classification and detection algorithms and generative learning that can be used to actually create models that in the extreme can render images. For example, as described further herein, a generative model can be configured for generating an image from a design clip that looks like that location on a wafer in a SEM image. This may be performed by 1) training the generative model with design clips and the associated actual SEM images from those locations on the wafer; and 2) using the model in inference mode and feeding it design clips for locations for which you want simulated SEM images generated. Such simulated images can be used as reference images in die-to-database inspection.

If the model(s) include one or more discriminative models, the discriminative model(s) may have any suitable architecture and/or configuration known in the art. Discriminative models, also called conditional models, are a class of models used in machine learning for modeling the dependence of an unobserved variable y on an observed variable x. Within a probabilistic framework, this is done by modeling the conditional probability distribution P(y|x), which can be used for predicting y from x. Discriminative models, as opposed to generative models, do not allow one to generate samples from the joint distribution of x and y. However, for tasks such as classification and regression that do not require the joint distribution, discriminative models can yield superior performance. On the other hand, generative models are typically more flexible than discriminative models in expressing dependencies in complex learning tasks. In addition, most discriminative models are inherently supervised and cannot easily be extended to unsupervised learning. Application specific details ultimately dictate the suitability of selecting a discriminative versus generative model.

A "generative" model can be generally defined as a model that is probabilistic in nature. In other words, a "generative" model is not one that performs forward simulation or rule-based approaches and, as such, a model of the physics of the processes involved in generating an actual image or output (for which a simulated image or output is being generated) is not necessary. Instead, as described further herein, the generative model can be learned (in that its parameters cart be learned) based on a suitable training set of data. As described further herein, such generative models have a number of advantages for the embodiments described herein. In addition, the generative model may be configured to have a deep learning architecture in that the generative model may include multiple layers, which perform a number of algorithms or transformations. The number of layers included in the generative model may be use case dependent. For practical purposes, a suitable range of layers is from 2 layers to a few tens of layers.

The deep learning described herein is a type of machine learning. Machine learning can be generally defined as a type of artificial intelligence (AI) that provides computers with the ability to learn without being explicitly programmed. Machine learning focuses on the development of computer programs that can teach themselves to grow and change when exposed to new data. In other words, machine learning can be defined as the subfield of computer science that "gives computers the ability to learn without being explicitly programmed." Machine learning explores the study and construction of algorithms that can learn from and make predictions on data—such algorithms overcome following strictly static program instructions by making data driven predictions or decisions, through building a model from sample inputs.

The machine learning described herein may be further performed as described in "Introduction to Statistical Machine Learning," by Sugiyama, Morgan Kaufmann, 2016, 534 pages; "Discriminative, Generative, and Imitative Learning," Jebara, MIT Thesis, 2002, 212 pages; and "Principles of Data Mining (Adaptive Computation and Machine Learning)" Hand et al., MIT Press, 2001, 578 pages; which are incorporated by reference as if fully set forth herein. The embodiments described herein may be further configured as described in these references.

In another embodiment, the model is a neural network. For example, the model may be a deep neural network with a set of weights that model the world according to the data that it has been fed to train it. Neural networks can be generally defined as a computational approach which is based on a relatively large collection of neural units loosely modeling the way a biological brain solves problems with relatively large clusters of biological neurons connected by axons. Each neural unit is connected with many others, and links can be enforcing or inhibitory in their effect on the activation state of connected neural units. These systems are self-learning and trained rather than explicitly programmed and excel in areas where the solution or feature detection is difficult to express in a traditional computer program.

Neural networks typically consist of multiple layers, and the signal path traverses from front to back. The goal of the neural network is to solve problems in the same way that the human brain would, although several neural networks are much more abstract. Modern neural network projects typically work with a few thousand to a few million neural units and millions of connections. The neural network may have any suitable architecture and/or configuration known in the art.

In a further embodiment, the model is a convolutional and deconvolution neural network. For example, the embodiments described herein can take advantage of learning concepts such as a convolution and deconvolution neural network to solve the normally intractable representation conversion problem (e.g., rendering). The model may have any convolution and deconvolution neural network configuration or architecture known in the art.

In one embodiment, the one or more simulations includes generating one or more simulated images for the specimen based on design information for the specimen, the electron beam based output includes one or more actual images of the specimen generated by the electron beam based subsystem, and the one or more simulated images illustrate how the specimen appears in the one or more actual images. In another embodiment, the one or more simulations include generating one or more simulated images for the specimen based on design information for the specimen and the optical based output, the electron beam based output includes one or more actual images of the specimen generated by the electron beam based subsystem, and the one or more simulated images illustrate how the specimen appears in the one or more actual images.

There may, therefore, be essentially two models that the system learns and executes. The first model may be a electron beam based die-to-database model that learns the transformation between electron beam based output and design. The simulations performed by this model allow both detection and classification of events detected based on electron beam output (since the simulations illustrate what the design should look like at that point in the process). The second model may be an optical SPPI model (SEM post-processing-based inspection model) that learns the triangular relationship between electron beam based output, optical based output, and design. Thus, once the models have been learned, the models can be used to generate a SEM image on an optical tool during post-processing based purely on the optical and design pattern. Such a simulated image can be verified by producing the corresponding electron beam based output using the electron beam based subsystem.

In one such example, the one or more simulations performed by the model may generate simulated image(s) illustrating how a specimen appears in actual image(s) generated by one of the subsystems described herein. In this manner, the simulated image(s) may represent images that may be generated of the specimen by an optical based subsystem or electron beam based subsystem described herein. In one such example, the input to the one or more simulations performed by the model may include design information for a specimen (e.g., any of the design data described further herein) and the output of the one or more simulations may include one or more simulated optical or electron beam images illustrating how the specimen on which the design information has been formed will appear in those images.

In some such embodiments, the one or more simulations performed by the model may be performed to generate one or more reference images that is/are used for inspection of specimen(s). In this manner, the embodiments described herein can enable advanced inspection algorithms such as die-to-database defect detection methods and/or algorithms in a manner that are extraordinarily efficient to apply in research and development and manufacturing scenarios. Enabling such defect detection is particularly valuable for electron beam based inspection where throughput is constrained by the rate of area coverage. By limiting image acquisition to "test" images only, throughput can be doubled or tripled versus currently used die-to-die inspection methods. The embodiments described herein may be further configured as described in U.S. patent application Ser. No. 15/353,210 by Bhaskar et al. filed Nov. 16, 2016, which is incorporated by reference as if fully set forth herein. For example, the embodiments described herein may be configured to perform single image detection as described in this patent application.

In some embodiments, detecting the defects includes determining if defects detected based on the optical based output are nuisances based on the electron beam based output. For example, the systems described herein may be configured for patch based storage (e.g., on the one or more virtual systems) and GPU computing (via the one or more computer subsystems). This architecture can store 100 to 1000 million patches per wafer in real time from an optical tool to an electron beam tool.

The patch based storage and GPU computing can be used to boost the optical signal to noise ratio. For example, the purpose for boosting the optical signal-to-noise ratio is to address a potential weakness in optical systems that is related to film thickness variations, LER, as well as prior layer defects. If necessary, the network can be retrained on every wafer to address wafer-to-wafer variations. In one such example, a few samples (in the 1K to 10K SEM image range) can be taken from a wafer in examination and then the model(s) can be trained to ignore the variations that the SEM says are nuisance. The SEM typically does not see prior layer defects or color variation. The rationale is that early on in the yield learning curve, there are a lot more process variations that need to be ignored.

In this manner, on the optical based subsystem, events may be detected that are defects. The nuisance rate is a key figure of merit for an inspection recipe. The nuisance rate indicates how well the inspector only finds what you care about. On the electron beam based system, the electron beam based output can be used to determine whether the events were in fact defects. The more effectively we can make detection on the optical based subsystem only include real defects, the lower the "nuisance rate" is, which is preferred.

This process may be more time consuming than standard line monitoring with an inspection tool (target to get results is about 8 hours), but it is still 100× to 1000× faster than pure electron beam based inspection. For example, perhaps 2 hours may be spent on the optical based subsystem and the remaining 4 to 6 hours may be spent on re-training and verification on the electron beam based subsystem. Since the patch images may be stored, they can rerun through the model(s). In particular, the presence of the stored data (patch images) will enable the optical based subsystem to adaptively retrain itself based on sampling a few (e.g., 100 to 1000) data points verified on the electron beam subsystem. Such a system will be far more robust to noise during the early discovery and RAMP process.

In another embodiment, the computer subsystem(s) are configured for performing the detecting the defects using the one or more models, and the one or more models are configured for selecting the at least two of the optical based output, the electron beam based output, the results of the one or more functions, and the results of the one or more simulations that are used for detecting the defects. Compared to traditional image fusion approaches, the advantage of using a model is enormous in terms of computer scalability. For example, in traditional processing, all channels of output may be kept in order to figure out a way to ensure that none of the signal is lost. In models, the hard work is done by the training. If it can exploit the additional channels, it will do so. If they don't add value, it will ignore them. This is a solution to the multiple channel, multiple costs explosion. In addition, the practical implementation of the multi-channel approach with conventional algorithms, simply will not happen. It is simply too difficult. Deep learning makes it practical because it teaches itself from examples.

The model(s) described herein may be used to assist with the defect-to-pixel ratio. For example, the ability of the model(s) to effectively learn the nominal LER and charging effects is a substantially powerful tool to make the defect-to-pixel ratio come closer to 1 in electron beam based inspection. There are two knobs one has to work with in electron beam based inspection. One knob is related to electron beam physics such as beam current/density or spot to sampling ratio which must be optimized. At smaller pixel sizes, one has to contend with more shot noise and hence more frame averaging. At higher beam currents, one may have the Coulomb effect to deal with. At larger pixel sizes, shot noise is less of a problem but resolution clearly suffers. In addition, another knob that is available is the electron beam based algorithms. For example, by leveraging the model(s) long term memory, the model(s) effectively ignore common noise sources such as LER and charging effects.

In a further embodiment, generating at least one of the optical based output and the electron beam based output are performed based on information for metrology markers on the specimen, and the one or more computer subsystems are configured to generate metrology information for the specimen based on the at least one of the optical based output and the electron beam based output generated for the metrology markers. Metrology markers can be used for pattern fidelity measurements (PFM). For example, in addition to the standard systematic defect types such as opens, shorts, protrusions, misshapen contacts, etc., the embodiments described herein will have the ability to detect missing and added patterns thanks to the design information. The system may also include metrology markers that will teach the system events that require a quantitative number such as line end pull backs more than 5 nm etc.

In this manner, the metrology markers may be a kind of special care area. It is straightforward with an electron beam based subsystem to go to the location of a marker and make a measurement to tell if the specification for a particular marker is met. With deep learning techniques discussed herein, this can be taken a step further to teach a model to flag likely "bad" sites during the optical inspection. This would allow the guiding of the electron beam based subsystem sampling toward the most likely locations to be failing. In addition, the system may include model(s) for sampling, image generation, and defect detection/classification and can comprehend metrology data both from substantially high throughput optical metrology (overlay, CD, films) tools as well as electron beam based metrology which may be enabled with dedicated in-die targets optimized to provide substantially high accuracy and precision at substantially high electron beam based subsystem throughput.

The model(s) described herein may be generated for specific specimens (e.g., specific wafers or reticles), processes, imaging parameters, etc. In other words, the models described herein may be specimen specific, process specific, imaging parameter specific, etc. In this manner, different models may be generated for different wafer layers. In addition, different models may be generated for different sets of imaging parameters (e.g., different imaging modes). Each of the different models may be generated with different training sets of data. Each of the different training sets of data may be generated as described further herein.

The embodiments described herein have a number of advantages described above. In addition, the embodiments described herein provide inspection solutions that have enormous potential for reducing the need for improvements in conventional electron beam inspectors while increasing the usefulness of current optical inspectors and will also create a unique market for electron beam inspectors. For example, the embodiments described herein can be used to allow substantially fast optical inspectors combined with relatively slow, substantially high resolution electron beam based tools (e.g., review and/or inspection tools) to provide substantially the same capability as electron beam based inspectors. In particular, the embodiments described herein provide a way to extend the sensitivity of optical based inspectors in ways that are not practical without the benefit of the model(s) and techniques described herein.

The embodiments described herein may also be configured for relatively fast pattern searching using a searchable database such as those described in U.S. Pat. No. 9,183,624 to Karsenti et al. issued on Nov. 10, 2015, which is incorporated by reference as if fully set forth herein. For example, a reference meta-data set of patterns of interest (POIs)/regions of interest (ROIs) having Bossung CDs as a function of focus, dose, overlay, etc. may be available as a hash table. The reference meta-data set hash table may be accessible at run time during any virtual or real process performed by the embodiments described herein. Example meta-data includes hash values associated with design polygons and expected attribute values. The meta-data may also include locations of instances of each pattern, like a relatively fast pattern search database. The attributes can be physical such as CD and can include statistical descriptors. The expected attribute values can be simulated and/or measurement CD at ADI and/or AEI. The attributes can further be specified for specific process conditions (e.g., focus, dose, overlay, oxide or other layer thickness, etc.). The patterns may be further specified by mask for multi-patterning lithography processes. The design intent layout data may be accessible for each instance of each POI/ROI in the hash table. In addition, a method for training the models described herein may be performed from a subset of the patterns referenced in the hash table.

In the embodiments described herein, the optical and electron beam based subsystems may be coupled to each other in a variety of different ways. For example, in one embodiment, the optical based subsystem and the electron beam based subsystem are only coupled to each other via the one or more computer subsystems. In one such example, as shown in FIG. 1, optical based subsystem 10 may be coupled to electron column 122 of the electron beam based subsystem via only computer subsystem 36, computer subsystem(s) 102, and computer subsystem 124. Therefore, computer subsystem(s) 102 may be common to the optical based subsystem and the electron beam based subsystem. In this manner, the electron beam based subsystem and the optical based subsystem may not necessarily be directly connected to each other except for data movement, which may be massive and may be facilitated by computer subsystem(s) 102 and/or virtual system(s) 108. As such, the system embodiments described herein (i.e., a hybrid inspector) may be in some sense a virtual inspector, where the electron beam and optical subsystems are not directly connected to each other except for data movement (which may be massive via the CCS or VI).

In another embodiment, the optical based subsystem and the electron beam based subsystem are only coupled to each other via the one or more computer subsystems and a common specimen handling subsystem. For example, the optical and electron beam based subsystems may be coupled by the computer subsystem(s) as described above. In addition, the optical based subsystem and the electron beam based subsystem may share common specimen handling system 136 and possibly load module 138, in which cassette 140 of specimens may be disposed. In this manner, specimens can come into a load module that is common to the optical and electron beam based subsystems, where they can be dispositioned to either (or both) of an optical based subsystem or an electron beam based subsystem. The specimens can also be moved substantially quickly between the electron beam and optical based subsystems.

In general, however, the optical based subsystem may be coupled to the electron beam based subsystem by a common housing (not shown), common specimen handling system 136, a common power source (not shown), computer subsystem(s) 102, or some combination thereof. The common housing may have any suitable configuration known in the art. For example, a housing may be configured to accommodate the optical based subsystem as well as the electron beam based subsystem. In this manner, the optical based subsystem and the electron beam based subsystem may be configured as a single unit or tool. The common specimen handling system may include any suitable mechanical and/or robotic assembly known in the art. The common specimen handling system may be configured to move the specimens between the optical based subsystem and the electron beam based subsystem in such a way that a specimen can be moved from the optical based subsystem directly into the electron beam based subsystem (or vice versa) without having to put the specimen back into its cassette or other container between the processes. The common power source may include any suitable power source known in the art.

The optical based subsystem and the electron beam based subsystem may be disposed laterally or vertically proximate to each other. For example, the system may be configured as a cluster of modules (or subsystems) that may each be configured to perform different processes. In addition, the optical based subsystem and the electron beam based subsystem may be disposed laterally or vertically proximate load module 138 of the system. The load module may be configured to support multiple specimens such as cassette 140 of wafers that are to be processed in the system. Robotic specimen handling system 136 may be configured to remove a specimen from the load module prior to measurement and/or inspection and to dispose a processed specimen into the load module. Furthermore, the optical based subsystem and the electron beam based subsystem may be disposed in other locations proximate each other such as anywhere a robotic common specimen handling system may fit such that a specimen may be moved between the subsystems. In this manner, common specimen handling system 136, a stage (not shown), or another suitable mechanical device may be configured to move a specimen to and from the optical based subsystem and the electron beam based subsystem.

Each of the embodiments of each of the systems described above may be combined together into one single embodiment.

Another embodiment relates to a computer-implemented method for detecting defects on a specimen. The method includes generating optical based output for a specimen by directing light to and detecting light from the specimen. The method also includes generating electron beam based output for the specimen by directing electrons to and detecting electrons from the specimen. In addition, the method includes receiving the optical based output and the electron beam based output generated for the specimen with one or more computer systems. The one or more computer systems include one or more virtual systems configured for performing one or more functions using at least some of the optical based output and the electron beam based output generated for the specimen. The one or more virtual systems are not capable of having the specimen disposed therein. One or more components are executed by the one or more computer systems, and the one or more components include one or more models configured for performing one or more simulations for the specimen. In addition, the method includes detecting defects on the specimen based on at least two of the optical based output, the electron beam based output, results of the one or more functions, and results of the one or more simulations.

Each of the steps of the method may be performed as described further herein. The method may also include any other step(s) that can be performed by the system, optical based subsystem, electron beam based subsystem, computer system(s), virtual system(s), component(s), and model(s) described herein. The system, optical based subsystem, electron beam based subsystem, computer system(s), virtual system(s), component(s), and model(s) may be configured according to any of the embodiments described herein. In addition, the method described above may be performed by any of the system embodiments described herein.

Figure 2:
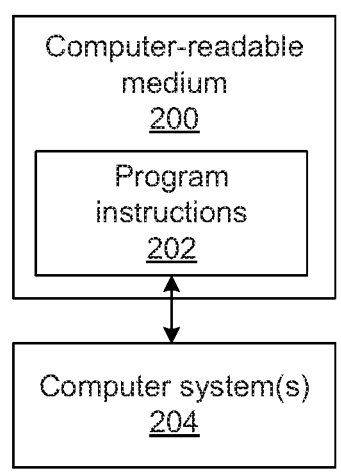
FIG. 2 is a block diagram illustrating one embodiment of a non-transitory computer-readable medium storing program instructions executable on one or more computer systems for performing one or more of the computer-implemented methods described herein.

An additional embodiment relates to a non-transitory computer-readable medium storing program instructions executable on one or more computer systems for performing a computer-implemented method for detecting defects on a specimen. One such embodiment is shown in FIG. 2. In particular, as shown in FIG. 2, non-transitory computer-readable medium 200 includes program instructions 202 executable on computer system(s) 204. The computer-implemented method may include any step of any method(s) described herein.

Program instructions 202 implementing methods such as those described herein may be stored on computer-readable medium 200. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), SSE (Streaming SIMD Extension) or other technologies or methodologies, as desired.

Computer system(s) 204 may be configured according to any of the embodiments described herein.

Further modifications and alternative embodiments of various aspects of the invention will be apparent to those skilled in the art in view of this description. For example, systems and methods for detecting defects on a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to detect defects on a specimen, comprising:

an optical based subsystem configured for generating optical based output for a specimen by directing light to and detecting light from the specimen;

an electron beam based subsystem configured for generating electron beam based output for the specimen by directing electrons to and detecting electrons from the specimen;

one or more computer subsystems configured for receiving the optical based output and the electron beam based output generated for the specimen, wherein the one or more computer subsystems comprise one or more virtual systems configured for performing one or more functions using at least some of the optical based output and the electron beam based output generated for the specimen, and wherein the one or more virtual systems are not capable of having the specimen disposed therein; and one or more components executed by the one or more computer subsystems, wherein the one or more components comprise one or more models configured for performing one or more simulations for the specimen; and wherein the one or more computer subsystems are further configured for detecting defects on the specimen based on at least two of the optical based output, the electron beam based output, results of the one or more functions, and results of the one or more simulations, wherein the one or more computer subsystems are further configured for performing said detecting the defects using the one or more models, and wherein the one or more models are further configured for selecting the at least two of the optical based output, the electron beam based output, the results of the one or more functions, and the results of the one or more simulations that are used for said detecting the defects.

2. The system of claim 1, wherein the one or more virtual systems are further configured for generating a reference for the specimen based on design information for the specimen, and wherein the reference is used for detecting the defects on the specimen.

3. The system of claim 1, wherein detecting the defects is further performed based on design information for the specimen in combination with the at least two of the optical based output, the electron beam based output, the results of the one or more functions, and the results of the one or more simulations.

4. The system of claim 1, wherein detecting the defects comprises comparing the optical based output to a first reference and comparing the electron beam based output to a second reference.

5. The system of claim 1, wherein the one or more virtual systems are further configured for storing all of the optical based output and the electron beam based output generated for the specimen indefinitely.

6. The system of claim 1, wherein the one or more virtual systems are further configured for generating information for the specimen without using the optical based output and the electron beam based output generated for the specimen and for storing the information generated by the one or more virtual systems in the one or more virtual systems.

7. The system of claim 1, wherein the one or more computer subsystems are further configured for receiving information for the specimen generated by another system, wherein the one or more virtual systems are further configured for storing the information, and wherein detecting the defects is further performed based on the stored information in combination with the at least two of the optical based output, the electron beam based output, the results of the one or more functions, and the results of the one or more simulations.

8. The system of claim 1, wherein the specimen comprises design for inspection structures, and wherein the one or more computer subsystems are further configured for extracting at least one of the optical based output and the electron beam based output generated for the design for inspection structures and performing one or more functions based on the extracted output.

9. The system of claim 1, wherein detecting the defects comprises volumetric inspection.

10. The system of claim 1, wherein detecting the defects comprises hyperspectral inspection.

11. The system of claim 1, wherein detecting the defects comprises multi-mode inspection.

12. The system of claim 1, wherein the one or more models are further configured for classifying the detected defects, and wherein the one or more computer subsystems are further configured for sampling the detected defects based on results of said classifying.

13. The system of claim 1, wherein the one or more components further comprise a single recipe configured for controlling at least the optical based subsystem and the electron beam based subsystem.

14. The system of claim 1, wherein the one or more computer subsystems are further configured for training the one or more models with information for defects detected in a process window qualification method.

15. The system of claim 1, wherein the one or more models comprise one or more deep learning based models.

16. The system of claim 1, wherein the one or more models comprise one or more machine learning based models.

17. The system of claim 1, wherein the one or more models comprise one or more discriminative models.

18. The system of claim 1, wherein the one or more models comprise one or more generative models.

19. The system of claim 1, wherein the one or more simulations comprise generating one or more simulated images for the specimen based on design information for the specimen, wherein the electron beam based output comprises one or more actual images of the specimen generated by the electron beam based subsystem, and wherein the one or more simulated images illustrate how the specimen appears in the one or more actual images.

20. The system of claim 1, wherein the one or more simulations comprise generating one or more simulated images for the specimen based on design information for the specimen and the optical based output, wherein the electron beam based output comprises one or more actual images of the specimen generated by the electron beam based subsystem, and wherein the one or more simulated images illustrate how the specimen appears in the one or more actual images.

21. The system of claim 1, wherein said detecting comprises determining if defects detected based on the optical based output are nuisances based on the electron beam based output.

22. The system of claim 1, wherein said generating at least one of the optical based output and the electron beam based output are performed based on information for metrology markers on the specimen, and wherein the one or more computer subsystems are further configured to generate metrology information for the specimen based on the at least one of the optical based output and the electron beam based output generated at the metrology markers.

23. The system of claim 1, wherein the optical based output is generated by the optical based subsystem with two or more different values of a parameter of the optical based subsystem.

24. The system of claim 1, wherein the electron beam based output is generated by the electron beam based subsystem with two or more different values of a parameter of the electron beam based subsystem.

25. The system of claim 1, wherein the specimen is a wafer.

26. The system of claim 1, wherein the specimen is a reticle.

27. The system of claim 1, wherein the optical based subsystem and the electron beam based subsystem are only coupled to each other via the one or more computer subsystems.

28. The system of claim 1, wherein the optical based subsystem and the electron beam based subsystem are only coupled to each other via the one or more computer subsystems and a common specimen handling subsystem.

29. A computer-implemented method for detecting defects on a specimen, comprising:
   generating optical based output for a specimen by directing light to and detecting light from the specimen;
   generating electron beam based output for the specimen by directing electrons to and detecting electrons from the specimen;
   receiving the optical based output and the electron beam based output generated for the specimen with one or more computer systems, wherein the one or more computer systems comprise one or more virtual systems configured for performing one or more functions using at least some of the optical based output and the electron beam based output generated for the specimen, wherein the one or more virtual systems are not capable of having the specimen disposed therein, wherein one or more components are executed by the one or more computer systems, and wherein the one or more components comprise one or more models configured for performing one or more simulations for the specimen; and detecting defects on the specimen based on at least two of the optical based output, the electron beam based output, results of the one or more functions, and results of the one or more simulations, wherein said detecting the defects is performed using the one or more models, and wherein the one or more models are further configured for selecting the at least two of the optical based output, the electron beam based output, the results of the one or more functions, and the results of the one or more simulations that are used for said detecting the defects.

30. A non-transitory computer-readable medium, storing program instructions executable on one or more computer systems for performing a computer-implemented method for detecting defects on a specimen, wherein the computer-implemented method comprises:

generating optical based output for a specimen by directing light to and detecting light from the specimen;

generating electron beam based output for the specimen by directing electrons to and detecting electrons from the specimen;

receiving the optical based output and the electron beam based output generated for the specimen with one or more computer systems, wherein the one or more computer systems comprise one or more virtual systems configured for performing one or more functions using at least some of the optical based output and the electron beam based output generated for the specimen, wherein the one or more virtual systems are not capable of having the specimen disposed therein, wherein one or more components are executed by the one or more computer systems, and wherein the one or more components comprise one or more models configured for performing one or more simulations for the specimen; and detecting defects on the specimen based on at least two of the optical based output, the electron beam based output, results of the one or more functions, and results of the one or more simulations, wherein said detecting the defects is performed using the one or more models, and wherein the one or more models are further configured for selecting the at least two of the optical based output, the electron beam based output, the results of the one or more functions, and the results of the one or more simulations that are used for said detecting the defects.

* * * * *